(12) United States Patent
Guenter et al.

(10) Patent No.: US 9,757,214 B2
(45) Date of Patent: Sep. 12, 2017

(54) DENTAL IMPLANT SOCKET ARRANGEMENT WITH ANNULAR RECESS

(71) Applicant: STRAUMANN HOLDING AG, Basel (CH)

(72) Inventors: Daniel Guenter, Basel (CH); Stephane Courvoisier, Basel (CH); Miodrag Lazic, Basel (CH); Florian Dalla Torre, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 0 days.

(21) Appl. No.: 14/897,404

(22) PCT Filed: Jun. 9, 2014

(86) PCT No.: PCT/EP2014/061941
§ 371 (c)(1),
(2) Date: Dec. 10, 2015

(87) PCT Pub. No.: WO2014/198682
PCT Pub. Date: Dec. 18, 2014

(65) Prior Publication Data
US 2016/0113738 A1 Apr. 28, 2016

(30) Foreign Application Priority Data
Jun. 10, 2013 (EP) ..................................... 13171317

(51) Int. Cl.
*A61C 8/00* (2006.01)

(52) U.S. Cl.
CPC ............ *A61C 8/006* (2013.01); *A61C 8/0022* (2013.01); *A61C 8/0066* (2013.01);
(Continued)

(58) Field of Classification Search
CPC ..... A61C 8/006; A61C 8/0018; A61C 8/0089; A61C 8/0022; A61C 8/0066; A61C 8/0068; A61C 8/0069
(Continued)

(56) References Cited

U.S. PATENT DOCUMENTS

| 5,076,788 | A  | * | 12/1991 | Niznick | ............... | A61C 8/0018 |
|           |    |   |         |         |                 | 433/173     |
| 6,733,291 | B1 | * | 5/2004  | Hurson  | ................ | A61C 8/0054 |
|           |    |   |         |         |                 | 433/173     |

(Continued)

FOREIGN PATENT DOCUMENTS

| EP | 1 419 746 A2 | 5/2004 |
| WO | 2005/037126 A1 | 4/2005 |

(Continued)

OTHER PUBLICATIONS

Aug. 28, 2014 International Search Report issued in International Patent Application No. PCT/EP2014/061941.
(Continued)

*Primary Examiner* — Pedro Philogene
*Assistant Examiner* — David C Comstock
(74) *Attorney, Agent, or Firm* — Oliff PLC

(57) ABSTRACT

A threaded dental implant to be screwed into a jawbone for supporting at least one abutment and/or a dental superstructure, and having a socket arrangement with a first section and a second section with respective geometrical profiles around a longitudinal center axis of the implant. The first section cooperates with the abutment for securing the abutment in a determined position in the implant. The second section cooperates with an insertion tool for screwing the implant into the jawbone. The first section includes an annular coronal contact surface on top of an opening centric at a coronal end of the implant, followed in an apical
(Continued)

direction by a first tapered section having a diameter decreasing in the apical direction, by a first cylindrical section, by first anti-rotational elements and by a threaded section.

16 Claims, 4 Drawing Sheets

(52) U.S. Cl.
CPC .......... *A61C 8/0069* (2013.01); *A61C 8/0089* (2013.01); *A61C 8/0068* (2013.01)

(58) Field of Classification Search
USPC ........................................................ 433/174
See application file for complete search history.

(56) References Cited

U.S. PATENT DOCUMENTS

| | | | | |
|---|---|---|---|---|
| 2002/0177105 A1* | 11/2002 | Engman | ................ | A61C 8/005 433/173 |
| 2010/0248181 A1* | 9/2010 | Kremer | ................ | A61C 8/0089 433/152 |
| 2010/0304329 A1* | 12/2010 | Heo | ..................... | A61C 8/0089 433/146 |
| 2011/0143316 A1* | 6/2011 | Olson | .................. | A61C 8/0089 433/147 |
| 2012/0196247 A1* | 8/2012 | Bugnard | .............. | A61C 8/0066 433/141 |

FOREIGN PATENT DOCUMENTS

| | | |
|---|---|---|
| WO | 2011/023750 A2 | 3/2011 |
| WO | 2013/003408 A1 | 1/2013 |

OTHER PUBLICATIONS

Dec. 15, 2015 International Preliminary Report on Patentability issued in International Patent Application No. PCT/EP2014/061941.

* cited by examiner

DENTAL IMPLANT SOCKET ARRANGEMENT WITH ANNULAR RECESS

FIELD OF THE INVENTION

The present invention relates in general to a threaded dental implant intended to be screwed into the jawbone for supporting at least one abutment and/or a dental superstructure and in particular to an improved socket arrangement of the dental implant cooperating on the one hand with an insertion tool and on the other hand with the abutment and/or a dental superstructure. Furthermore, the present invention relates to the insertion tool comprising retention means being adapted to engage with a corresponding annular retention recess within the socket arrangement of the implant.

PRIOR ART

As known in the art, a threaded dental implant intended to be screwed into the jawbone for supporting at least one abutment and/or a dental superstructure must have a certain socket arrangement with first sections comprising lateral contact surfaces and an upper coronal contact surface and an inner threaded section, such that the abutment can be fixed for a long time in a determined stable position. Furthermore, as known in the art, the threaded dental implant needs to be screwed into the jawbone with certain torque forces of up to approximately 150 Ncm. During this screwing operation the problem has to be faced that the insertion tool, which is for instance an Allen wrench engaging with an Allen socket as part of a second section of the socket arrangement, could cause material welding or a deformation within respective lateral second contact surfaces of the Allen socket. Thus, if the same lateral contact surfaces would be used for the positioning of the abutment and/or a dental superstructure and the engagement with the insertion tool, or in other words if the first contact surfaces would be the same as the second contact surfaces, the abutment would not fit anymore into the implant in the determined position, due to changes in the socket. In other words, the first sections of the socket arrangement must not be damaged at all.

The implant is positioned in the patient's mouth, namely in a drill hole in the jawbone of the patient, by connecting it to the insertion tool, in particular by inserting an apical part of the insertion tool into the implant and keeping it with a finger on the insertion tool.

WO 2013 003 408 discloses a threaded dental implant with a socket arrangement having an annular recess on an apical side below the first and second sections of the socket arrangement engageable with laterally slightly extending tips of the insertion tool, such that the implant is retained by a frictional force of the extending tips. However, the external diameter of the tips has to be manufactured extremely precise, such that the tips reliably engage with the recess and such that the retaining forces are reliably kept from getting too high. Accordingly, a disengagement of the insertion tool from the implant could become critical. Taking into account the dimensions of a contact area and of a flexible structure with a small diagonal diameter and a small length in longitudinal direction, tolerances for the manufacturing of the recess and the tips of the insertion tool are technically difficult to achieve and costly. In effect little changes in the tolerances can result in a too low or too high friction, such that the implant may not retained by the insertion tool or such that a disengagement of the insertion tool is problematical.

For the sake of clarity it is mentioned that the wording "implant" stands herein for dental implant or threaded dental implant. Further, for the sake of clarity it is mentioned that the wording "abutment" stands herein also for a superstructure being connected to at least one implant and carrying one or more artificial teeth or crowns, for instance a dental bridge.

SUMMARY OF THE INVENTION

The objective of the invention is to overcome the shortcomings explained above and to provide a threaded dental implant with a socket arrangement cooperating with an insertion tool for screwing the implant into a jawbone and the insertion tool, wherein the socket arrangement provides first retention means cooperating with second retentions means of the insertion tool, such that a retention force is provided between the implant and the insertion tool, strong enough that the implant is retained during an insertion in the patient's mouth, but also with little more force to be overcome, such that the insertion tool is disengageable without damaging the position of the implant in the jawbone, and this with as large as possible manufacturing tolerances for the first and the second retention means. The first retention means should be arranged within the socket arrangement keeping connecting force transmitting socket surfaces to the abutment and to the insertion tool as big as possible, consuming as little space as possible.

The above objectives as well as further objectives which will also become apparent from the following description are achieved by the features of a threaded dental implant with an annular retention recess and by an insertion tool carrying respective retention means cooperating with the retention recess, as set out in the independent claims 1 and 15, respectively. Additional features and characteristics of the invention are set out in the dependent claims.

Advantageously the embodiment of the present invention provides the dental implant with a socket arrangement with a first section and a second section with respective geometrical profiles of contact surfaces, wherein the first section is devised to cooperate with the abutment for securing the abutment in a determined position in the implant and the second section is devised to cooperate with the insertion tool for screwing the implant in, and wherein the first and the second sections are completely separated from each other. The first are second sections as used in the context of the present description and in the appended claims are rather intended as functional sections for cooperating with the abutment and the insertion tool, respectively. Nevertheless, the first section is not intended to be a geometrically contiguous entity. Same applies for the second section. Also the first and second sections may have overlapping sections long the height of the is longitudinal axis of the implant.

The first section comprises an annular coronal contact surface on top of an opening centric at a coronal end of the implant, followed in an apical direction by a first tapered section having a diameter decreasing in the apical direction, by a first cylindrical section (8), by first anti-rotational means and by a threaded section.

The second section comprises a flat horizontal platform perpendicular to the longitudinal axis and apically below the first cylindrical section, and further followed in an apical direction by second anti-rotational means, wherein the second section further comprises an annular retention recess positioned around the longitudinal center axis and between the first cylindrical section and the flat horizontal platform, the retention recess having at least in part a diameter larger than the diameter of the first cylindrical section of the annular coronal contact surface and being adapted to engage with a retention means of the insertion tool.

The annular retention recess which is positioned in apical direction directly behind the first cylindrical section is provided at an undercut which is also advantageous for manufacturing purposes in order to be able to provide the flat horizontal platform following the first cylindrical section in apical direction. Thus an additional space consumed by the annular retention recess is kept very small resulting in still large areas for the first section and the second section of the socket arrangement which are the force transmitting parts of the socket arrangement.

Preferred embodiments of the invention provide the annular retention recess with a second tapered section which is tapered outwardly starting at an apical end of the first cylindrical section seen in the apical direction. Or seen from an apical end in coronal direction the second tapered section is then tapered inwardly and merges with its truncated conical end into the first cylindrical section, such that an elastic O-ring or split C-ring attached to the insertion tool gets continuously squeezed when the insertion tool is pulled out of the implant, in the longitudinal coronal direction. Thus, abrupt forces are avoided during the process of pulling the insertion tool out of the implant while the implant gets disengaged from the insertion tool, or vice versa. Accordingly, as the O-ring or split C-ring is moved along the second tapered section in coronal direction, the retention force increases continuously until the O-ring or split C-ring reaches the first cylindrical section. On the first cylindrical section the retention force is constant due to the fact that the O-ring or split C-ring is not squeezed anymore and only a same friction force occurs. When the O-ring or split C-ring reaches at the coronal end of the first cylindrical section an apical end of the first tapered section and glides in coronal direction along the first tapered section, tapered outwardly in coronal direction, the O-ring or split C-ring expands and the friction forces get smaller. Thus, an abrupt change of the retention force or the pulling out force is avoided, as it could occur if the annular retention recess would not be tapered in coronal direction, such as according to the prior art. Avoiding abrupt changes in the pulling out force of the insertion tool or the O-ring or split C-ring, respectively, results in avoiding hits of the insertion tool against one of the contact surfaces of the first sections of the socket arrangement.

Advantageously a preferred O-ring or split C-ring carried on the insertion tool is made of plastic or rubber material, such that the first cylindrical section cannot become damaged by the much softer material of the O-ring or split C-ring.

Further preferred embodiments provide the annular retention recess with an additional second cylindrical section below the second tapered section, from a view in the apical direction. The second cylindrical section advantageously provides a section of the annular retention recess where the O-ring or split C-ring can expand to a maximum and wherein the O-ring or split C-ring can be slightly tilted in respect to the longitudinal center axis of the implant.

The dimension and the inclination angle according to the invention of the first tapered section are also advantageous features for the finding of the insertion tool or the abutment during an insertion into an inner bore of the implant. The dimension and the inclination angle of the second tapered section according to the invention provide for advantages for the retention force and the force for the disengagement between the insertion tool and the implant.

Preferably parts of the first and the second sections of the socket arrangement having an anti-rotational functionality are arranged within a same height along the longitudinal center axis, such that space is saved and the remaining areas of the parts of the first and the second sections remain as large as possible.

An octagonal cross-sectional arrangement of first contact surfaces of the first sections provides a particularly advantageous aspect of the invention, as the outer surface of an octagon is larger as compared with a surface of a hexagon with a same height. Thus, an octagonal cross-sectional socket with the respective eight first contact surfaces has a larger contact area engaging with the abutment than a hexagonal cross-sectional socket and still good enough anti-rotational resistance for the abutment on the implant. By the larger first contact surfaces higher lateral forces between the abutment and the implant can be applied without deforming the implant. In respect to the first contact surfaces a torque force around the longitudinal center axis of the implant is much lower than for the second contact surfaces, as the abutment does not apply a torque as high as the insertion tool does. The torque transmitting surface for the insertion tool increases with the number of notches and respective ridges extending in the longitudinal direction from the respective coronal cross-sectional notches and having the respective second contact surfaces. Thus also a number of up to eight notches can be devised according to the torque for screwing in the implant, and/or according to the material strength and thickness of the remaining coronal lateral sidewall of the implant at the height of the first and second contact surfaces.

The invention is set forth and characterized in the main claims, while dependent claims describe other advantageous characteristics of the invention.

Preferred embodiments according to the present invention are disclosed in the following drawings and in the detailed description but it shall not be limiting the invention.

DETAILED DESCRIPTION OF A PREFERENTIAL EMBODIMENT OF THE INVENTION

Figure 1:
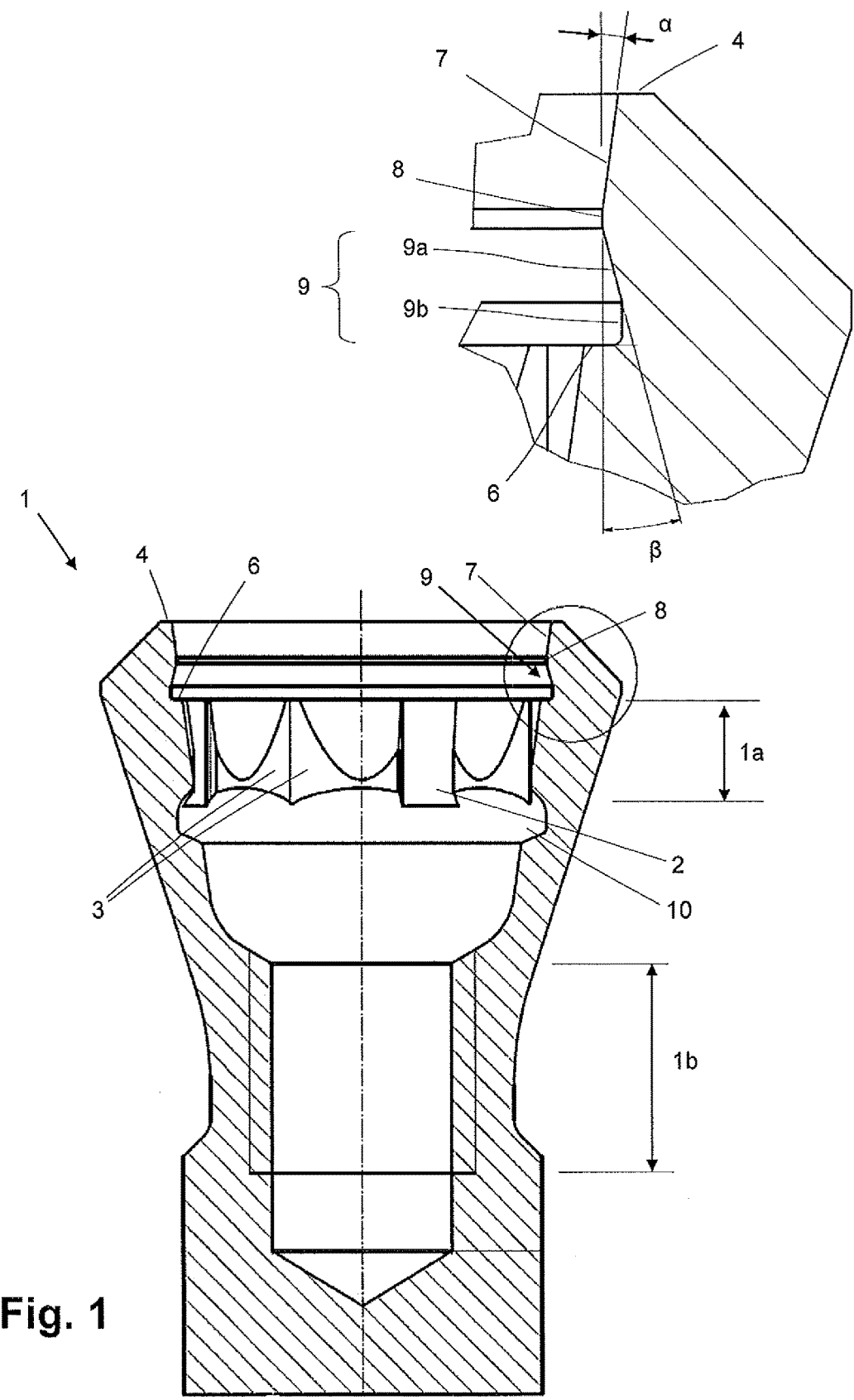
FIG. 1 is a cross-sectional side view of a threaded dental implant depicting from a coronal view in apical direction: an annular coronal contact surface, a first tapered section, an annular retention recess, a flat horizontal platform, an anti-rotational section, an undercut, and an internal threaded section. Above is depicted a magnified cross-sectional side view of the annular coronal contact surface, the first tapered section, the annular retention recess comprising a second tapered section and a transition section, and the flat horizontal platform.

FIG. 1 shows in a lower part of the figure a cross-sectional side view of a preferred embodiment of a threaded dental implant 1 having an upper annular coronal contact surface 4 being preferably perpendicular to a longitudinal center axis of the implant 1. The upper annular coronal contact surface 4 comprises a centric opening followed by a bore in apical longitudinal direction, wherein the bore along its longitudinal axis is laterally extended by lathing and/or milling. The bore starts, as seen from its coronal end, at the perpendicular annular coronal contact surface 4. Further apically of the contact surface 4 there is provided a first tapered section 7 which is tapered inwardly in apical direction. Preferably the first tapered section 7 is substantially a truncated cone with a first inclination angle. The first tapered section 7 is followed by a first cylindrical section 8, in apical direction. The first cylindrical section 8 is then followed by an annular retention recess (first undercut) 9 in apical direction. The annular retention recess 9 in the apical direction is then followed by a flat horizontal platform 6 being perpendicular to the longitudinal center axis and having a shape of an annular horizontal platform with an opening in the center, where the bore like hole continues in apical direction. The opening of the flat horizontal platform 6 has an inner diameter or distance between opposite sides which is smaller than the first cylindrical section 8, such as to provide for an annular inside step towards the longitudinal center axis.

The above part of FIG. 1, as a magnified cross-sectional side view of a coronal part of the implant 1 circled in the picture below, depicts the annular retention recess 9 in more detail. The annular retention recess 9 is preferably devised as a second tapered section 9a, tapered outwardly in apical direction with substantially a second inclination angle, and further includes a transition section 9b apically following the second tapered section 9a and connecting the apical end of the second tapered section 9a with the flat horizontal platform 6. Preferably the second tapered section 9a is shaped as a truncated cone. Preferably the transition section 9b is shaped partly or completely as a second cylindrical section with a diameter equal to that of the apical end of the second tapered section 9a. Preferably the transition section 9b is shaped partly as the second cylindrical section with the diameter equal to that of the apical end of the second tapered section 9a followed, in apical direction, by a curved section merging into the flat horizontal platform 6.

The opening of the flat horizontal platform 6 is then followed, in apical direction, by an anti-rotational section 1a comprising first contact surfaces 3 as anti-rotational means for an inserted abutment or dental superstructure, and second contact surfaces 2a, 2b building notches 2 or ridges as anti-rotational means for an insertion tool 11, inserted in the implant 1.

Further, the anti-rotational section 1a is preferably followed in the apical direction by a second undercut 10, such as to free the first contact surfaces 3 and the second contact surfaces 2a, 2b towards the apical end, in order to allow a complete insertion of the abutment or the insertion tool until the one or the other abuts against the annular coronal contact surface 4 or the flat horizontal platform 6, respectively. The second undercut 10 or the anti-rotational section 1a is then followed by an internal thread within an internal threaded section 1b, such as to allow the abutment or the dental superstructure to become fixed on the implant 1 by a screw.

Preferably the first inclination angle α (alpha) of the first tapered section 7 which is shaped substantially conical is about 5°-15°, or even more preferred about 8° with a tolerance of +/−1°, with respect to the longitudinal center axis of the implant 1. This angle has "finding" functionality, such the abutment, the dental superstructure of the insertion tool 11 find better into the inner bore or bore like recess during insertion into the implant 1 and it has preferably a sealing functionality as well. During the insertion of the insertion tool 11 into the implant 1, the first tapered section 7 allows a soft increase of a pushing and engaging force between the insertion tool 11 and the implant 1, because a retention means 12 of the insertion tool becomes squeezed and reduced in its diameter along the way of the insertion (see FIG. 4).

Because the inner diameter of the flat horizontal platform 6 is smaller than the diameter of the first cylindrical section 8, the retention means 12 of the insertion tool 11 are adapted to fit squeezed through the first cylindrical section 8 but to be kept back from the flat horizontal platform 6, or vice versa.

The flat horizontal platform 6 has additional functionality working as an annular step and rotational turning point during the insertion of the torque force transmitting ribs 13 of the insertion tool 11 into the notches 2 or ridges, respectively. Therefore the apical ends of the ribs 13 are kept back and may be rotated until they are flush with the notches 2 or ridges, respectively, and may slip into the ridges.

For the sake of clarity, the wording "bore" stands for any bore like hole or recess, also having a changing diameter or in some parts being conical or polygonal along the longitudinal center axis of the implant 1.

Preferably the second inclination angle β (beta) of the second tapered section 9a which is shaped substantially conical is between 10° and 20°, or more preferably between 14° and 16°, with respect to the longitudinal axis. The second inclination angle about 15° has turned out to be most preferable, such as to have a soft increase of a retention force during pulling out the insertion tool 11 of the implant 1, wherein an O-ring or split C-ring gets squeezed not to rapidly and too much, relative to an expanded position at the apical end of the second tapered section 9a. Preferably a diameter at the apical end of the second tapered section 9a is about the diameter of the opening of the annular coronal contact surface 4, such that the retention means 12 of the insertion tool may be inserted at the opening of the annular coronal contact surface 4 at the beginning with no force, and may expand after the engagement in a longitudinal height at the apical end of the second tapered section 9a substantially to its original size.

Preferably, the second cylindrical section 9b has the same height as that of the retention means 12 and the retention means 12 are in the form of an elastic O-ring or split C-ring with a certain thickness.

Preferably the second tapered section 9a has a height along the longitudinal axis of 1.5-2.5 times of the height of the transition section 9b.

Generally, the threaded dental implant 1 is intended to be screwed into a jawbone for supporting at least the abutment and/or the dental superstructure, and therefore it has a socket arrangement comprising a first section devised to cooperate long time with the abutment for securing the abutment in a determined position on and in the implant (1), and a second section devised to cooperate temporarily with the insertion tool (11) for screwing the implant (1) into the jaw bone.

The first section comprises the annular coronal contact surface 4, the first tapered section 7, the first cylindrical section 8, the first anti-rotational means being the first contact surfaces 3, and the internal thread within the threaded section 1b.

The second section comprises the annular retention recess 9, the flat horizontal platform 6 and the second anti-rotational means. The second anti-rotational means are preferably embodied as the notches 2 or ridges with their second contact surfaces 2a, 2b.

Preferably, the first and the second sections of the socket arrangement are completely separated from each other, such that the respective first contact surfaces 3 and the second contact surfaces 2a, 2b are separated from each other even if they are intersecting each other geometrically.

Basically the first contact surfaces 3 are arranged around and parallel to the longitudinal center axis forming a cross-sectional shape perpendicular to the longitudinal center axis of a regular polygon. In addition, it is also imaginable that sections 3b (in the following also called truncated conical sections) of the first contact surfaces 3 are arranged inclined or tapered in the apical direction and around the longitudinal center axis substantially forming together a truncated pyramidal shape with a cross-section of a regular polygon. However, the contact with the abutment occurs at the sections of the first contact surface 3 which are parallel to the longitudinal axis of the dental implant but not at the inclined parts or the truncated conical sections 3b. Preferably the first contact surfaces 3 are intersected by the second anti-rotational means for the insertion tool 11, wherein the second anti-rotational means are shaped as the ridges extending as well laterally of the first contact surfaces 3 as in apical direction.

The following FIGS. 2-5 show further modifications which can be applied to the first preferred embodiment according to FIG. 1 partly or in all.

Figure 2:
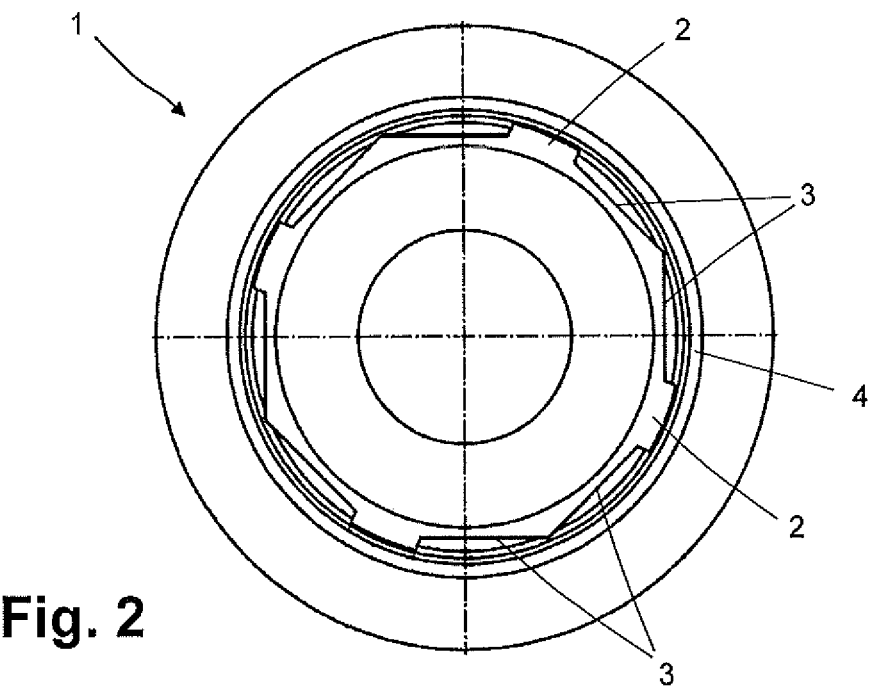
FIG. 2 is a top view drawing of another embodiment of the threaded dental implant reduced to a socket arrangement with first contact surfaces and second contact surfaces of the anti-rotational section, wherein the second contact surfaces have a shape of four notches or ridges having the rectangular cross-sectional shape.

FIG. 2 depicts from a top view a preferred embodiment of the threaded dental implant 1, depicting the annular coronal contact surface 4, the notches 2 as end parts of the extended ridges in longitudinal direction, and the first contact surfaces 3 having a substantially regular polygonal shape. The first contact surfaces 3, which have a form of the regular polygon and in particular of a regular octagon, are intersected, from a cross-sectional view, by the notches 2. The notches 2 are the torque force transmitting anti-rotational means engaging with the insertion tool 11. At this point it should be noted that in the context of the present invention the notches 2 are defined as cross-sections in the ridges, the ridges extending in the longitudinal direction of the dental implant 1. In other words the wording the notches 2 represent cross-sectional lines of the ridges, and the ridges extend from the cross-sectional respective notches 2 in the longitudinal direction with or without an inclination.

Figure 3:
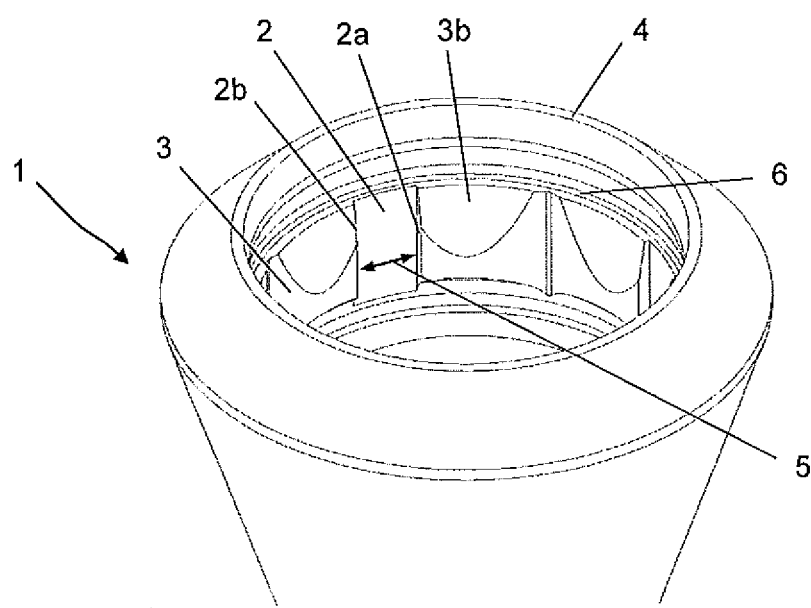
FIG. 3 is a perspective view of the embodiment of FIG. 2.

FIG. 3 shows in a perspective view the threaded dental implant 1 according to FIG. 2, with the notches 2, which are formed as the ridges in the longitudinal direction preferably starting from flat horizontal platform 6. The lateral sides of the notches 2 or ridges, respectively, are the second contact surfaces for transmitting the torque forces of the insertion tool or of the ribs 13 thereof, respectively. The first contact surfaces 3 show further, as mentioned, the preferred truncated conical sections 3b which are slightly cut out or eroded, respectively, from a coronal part of the first contact surfaces 3, wherein the truncated conical sections 3b have a diameter of opposed sides which is slightly larger than the inner distance between opposed sides of the first surfaces 3, with respect to a certain height along the longitudinal axis. The diameter of the truncated conical sections 3b between the opposed sides of the truncated cone is smaller than the distances between the edges of the regular polygon, such that the edges of the regular polygon with an additional area of the first surfaces 3 remain in place and are not cut out.

Figure 4:
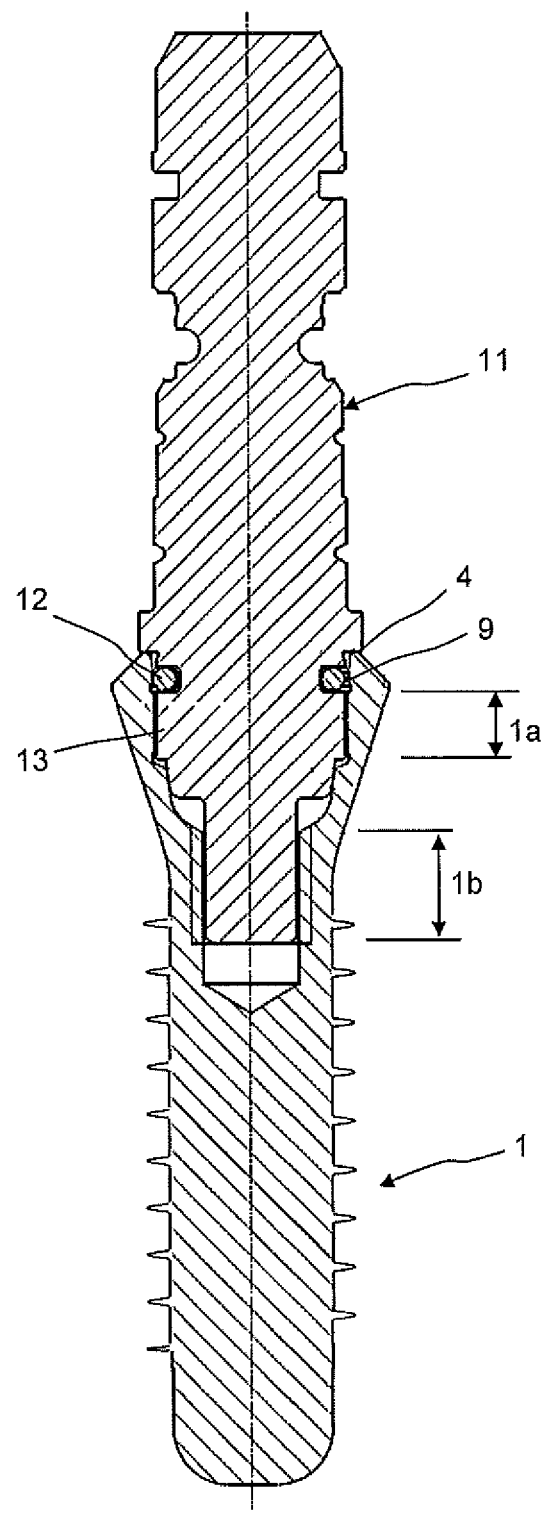
FIG. 4 is a cross-sectional side view drawing of a simplified threaded dental implant, in which an insertion tool is engaged.

FIG. 4 shows a cross-sectional side view of a simplified version of the threaded dental implant 1 with the insertion tool 11, wherein the insertion tool 11 or a transfer piece (hereinafter for the sake of simplicity only designated as insertion tool 11) is engaged with a coronal portion thereof. The outer part of an apical portion of the implant 1 carries an external thread. The external thread comprises preferably self-cutting means as for instance sharp recesses or grooves, not shown, such that the implant 1 can cut its thread into a jawbone. For the insertion of the implant 1 in the jawbone the insertion tool 11 is temporarily connected with the implant 1 for the insertion. Preferably the jawbone comprises an appropriate hole for the implant 1. During the insertion of the implant in the jawbone there occur torques of up to about 150 Ncm which have to be transmitted from the insertion tool 11 to the implant. After the implant 1 has been inserted in the jawbone and after engraftment, the abutment or the dental superstructure, which is not shown herein, is placed and fixed onto the coronal end of the implant 1. The positioning of the abutment must be possible precisely and in a determined height as well as in a defined rotational position or angle.

The implant 1 comprises the socket arrangement with the first and the second sections within the anti-rotational section 1a of the socket arrangement. As shown, the internal threaded section 1b is preferably also used as a guiding and axial stabilizing means for the insertion tool 11.

The insertion tool 11 comprises the retention means 12, being preferably an O-ring or split C-ring. Preferably the retention means 12 is made of a material, such as metal as for instance titanium, steel, a steel compound, or such as plastics as for instance Rubber, Silicon or other rubber materials. Preferably the material of the retention means 12 is much softer than the material of the implant 1, such that the implant 1 does not get any dents from the retention means 12. The retentions means 12 shown as O-ring or split C-ring is positioned within the annular retention recess 9 of the implant 1.

Preferably the retention means 12 are shaped and adapted to be engageable and disengageable with the inner annular retention recess 9, such that the retention force on said implant 1 is exerted during insertion in the patient's mouth, and that the disengagement force is small enough to not affect the position of the implant 1 during a disengagement of the insertion tool 11 from the implant 1.

Figure 5:
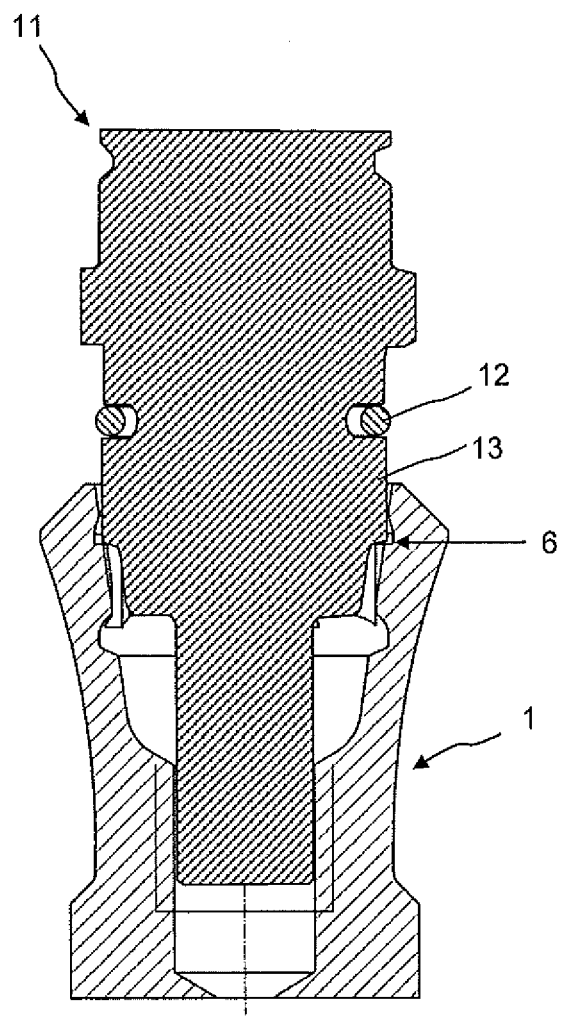
FIG. 5 is a cross-sectional side view of an embodiment of the threaded dental implant similar to that of FIG. 1, wherein the insertion tool is inserted partly, wherein ribs of the insertion tool, which are torque force transmitting parts, are sitting with their apical ends on the flat horizontal platform for finding the respective notches or ridges with the second contact surfaces thereof.

FIG. 5 depicts from a cross-sectional side view the implant 1 in which the insertion tool 11 is inserted partly in the coronal part of the implant 1, such that the ribs 13 of the insertion tool 11 are moving rotationally on the flat horizontal platform 6, until they are flush with the notches 2 or ridges of the second sections of the socket arrangement.

Preferably the ridges have a cross-sectional shape in a plane and at the beginning of the flat horizontal platform 6, said cross-sectional shape corresponding to the laterally extending notches 2 extending in the apical direction as the ridges. Preferably each of the ridges comprises respective second contact surfaces 2a, 2b at opposite sides and substantially in a tangential direction with respect to the longitudinal center axis. The second contact surfaces 2a, 2b extend from the coronal end to an apical end of the second anti-rotational means and are adapted to transmit the torque forces from the ribs 13 of the insertion tool 11.

Preferably the regular polygon is an octagon. Preferably the notches 2 are shaped as squares or rectangles or triangles or trapezoids with respective second surfaces 2a, 2b.

Preferably the notches 2 and the second surfaces 2a, 2b, respectively, are shaped to be substantially perpendicular to the torque forces of the ribs 13, the torque forces having respective vectors which are substantially tangential with respect to the longitudinal center axis of the insertion tool 11 or the implant 1, respectively. Said torque forces occur during a process of screwing the implant 1 into the jawbone or after an incorporation out of the jawbone. Preferably the second surfaces 2a, 2b are devised perpendicular to the torque forces with a tolerance of +/−10°.

Preferably the polygon is an octagon intersected by a number of four or six notches 2. Another preferred embodiment of the implant has a number of eight notches.

Preferably the notches 2 or ridges, respectively, are furthermore laterally shaped as circular arcs laterally slightly curved, which comprise at least one laterally curved surface being comprised between opposed sides of the second contact surfaces 2a, 2b of a respective notch 2, the circular arcs having a diameter of the opposed circular arcs of respective opposed notches 2, with respect to the longitudinal center axis of the implant 1.

Preferably, in all above embodiments, the socket arrangement is devised centric and along the longitudinal axis of the implant 1, such that both the first contact surfaces 3 and the second contact surfaces 2a, 2b are arranged to be axis symmetrical to the longitudinal axis.

LIST OF REFERENCE NUMERALS

1 dental implant
1a anti-rotational section
1b internal threaded section
2 notch
2a, 2b second contact surface
3 first contact surfaces
3b truncated conical sections
4 annular coronal contact surface
5 notch width
6 flat horizontal platform
7 first tapered section
8 first cylindrical section
9 annular retention recess or first undercut
9a second tapered section
9b transition section
10 second undercut
11 insertion tool
12 retention means
13 ribs
α, β angles

The invention claimed is:

1. Threaded dental implant intended to be screwed into a jawbone for supporting at least one abutment and/or a dental superstructure, and having a socket arrangement with a first section and a second section with respective geometrical profiles around a longitudinal center axis of the implant, wherein the first section is devised to cooperate with the abutment for securing the abutment in a determined position in the implant, wherein the second section is devised to cooperate with an insertion tool for screwing the implant into the jawbone, the first section comprising an annular coronal contact surface on top of an opening centric at a coronal end of the implant, followed in an apical direction by a first tapered section having a diameter decreasing in the apical direction, by a first cylindrical section, by first anti-rotational means and by a threaded section;

the second section comprising a flat horizontal platform perpendicular to the longitudinal center axis and apically below the first cylindrical section, and further followed in apical direction by second anti-rotational means, wherein the second section further comprises an annular retention recess positioned around the longitudinal center axis and between the first cylindrical section and the flat horizontal platform, the retention recess having at least in part a diameter larger than a diameter of the first cylindrical section of the annular coronal contact surface and being adapted to engage with a retention means of the insertion tool.

2. Dental implant according to claim 1, wherein the retention recess comprises a second tapered section starting at an apical end of the first cylindrical section with a diameter equal to that of the first cylindrical section and then expanding in apical direction to an apical end of the second tapered section, wherein the apical end of the second tapered section is followed by a transition section, wherein the transition section in the apical direction merges into the flat platform.

3. Dental implant according to claim 2, wherein the second tapered section is shaped as a cone.

4. Dental implant according to claim 2, wherein the second tapered
section has an inclination angle (β) between 10° and 20°, with respect to the longitudinal center axis; and/or
wherein the second tapered section has a height along the longitudinal center axis of 1.5-2.5 times of a height of the transition section.

5. Dental implant according to claim 4, wherein the first tapered section is shaped substantially conical with an inclination angle (α) of 5°-15° with respect to the longitudinal center axis.

6. Dental implant according to claim 2, wherein the transition section comprises
a second cylindrical section following the apical end of the second tapered section, and/or
a curved section following the second cylindrical section and being tapered in the apical direction with a diameter decreasing in an apical direction until merging into the flat platform,
wherein the second cylindrical section and/or the curved section are adapted to the retention means.

7. Dental implant according to claim 1, wherein the first anti-rotational means for the securing the abutment and the second anti-rotational means for cooperating with the insertion tool are arranged within an anti-rotational section of height along the longitudinal center axis.

8. Dental implant according to claim 1, wherein the first anti-rotational
means comprise first contact surfaces which are arranged around and parallel to the longitudinal center axis, the first contact surfaces including truncated conical sections with an inward taper in an apical direction and around the longitudinal center axis, the first contact surfaces substantially forming together a cross-section of a regular polygon; and/or the first contact surfaces are intersected by the second anti-rotational means for the insertion tool, wherein the second anti-rotational means are shaped as ridges extending as well laterally of the first contact surfaces as in apical direction.

9. Dental implant according to claim 8, wherein the ridges have a cross-sectional shape in a plane and at the beginning of the flat horizontal platform as laterally extending notches extending in the apical direction as the ridges,
   wherein the ridges comprise each at opposite sides in substantially tangential direction with respect to the longitudinal center axis second contact surfaces, the second contact surfaces extending from the coronal end to an apical end of the second anti-rotational means and being adapted to transmit torque forces from torque force transmitting ribs of the insertion tool to the implant.

10. Dental implant according to claim 9, wherein the notches are positioned at sides or at corners of the regular polygon.

11. Dental implant according to claim 9, wherein the regular polygon is an octagon and/or
   wherein the notches are shaped as squares or rectangles or triangles or trapezoids.

12. Dental implant according to claim 9, wherein the polygon is an octagon intersected by a number of four or six notches.

13. Dental implant according to claim 9, wherein the number of notches is eight.

14. Dental implant according to claim 8, wherein said second contact surfaces are angled perpendicularly to torque forces applied by respective contact surfaces of the ribs of the insertion tool during a process of screwing the implant into the jawbone; or wherein said second contact surfaces are angled with a tolerance perpendicularly to the torque forces applied by respective contact surfaces of the ribs of the insertion tool during the process of screwing the implant into the jawbone, wherein the tolerance is +/−10°.

15. Insertion tool in combination with the dental implant according to claim 1, the insertion tool having an apical and force transmitting part which is engageable with the dental implant, the insertion tool having:
   ribs in longitudinal direction of the insertion tool, the ribs corresponding to and engageable with second anti-rotational means or second contact surfaces of notches or ridges of the implant, said notches or ridges of the implant providing the second anti-rotational means for engagement with the insertion tool for transmitting insertion torque forces; and
   a form fitting into a socket arrangement with first sections of the implant, wherein said first sections are for cooperating with the abutment for securing the abutment in a determined position in the implant, said form of the insertion tool being configured such that it keeps a distance to the first sections or such that it comprises round parts at the first sections such that no torque force is transmitted to said first sections; and
   an apical part of the insertion tool being insertable in the implant and carrying retention means, the retention means being shaped and adapted to be engageable and disengageable with an inner annular retention recess positioned around the longitudinal center axis of the implant, such that a retention force on said implant is exerted during insertion in the patient's mouth, and such that a disengagement force is small enough to not affect the position of the implant during a disengagement of the insertion tool from the implant.

16. Insertion tool according to claim 15, wherein the retention means is an elastic O-ring or a split C-ring, and/or
   wherein the elastic O-ring or split C-ring is made of metal, or is made of a plastics.

* * * * *